US005742943A

United States Patent [19]

Chen

[11] Patent Number: 5,742,943
[45] Date of Patent: Apr. 28, 1998

[54] SLIP-COATED ELASTOMERIC FLEXIBLE ARTICLES AND THEIR METHOD OF MANUFACTURE

[75] Inventor: Mao C. Chen, Arlington, Tex.

[73] Assignee: Johnson & Johnson Medical, Inc., Arlington, Tex.

[21] Appl. No.: 699,032

[22] Filed: Aug. 19, 1996

Related U.S. Application Data

[63] Continuation-in-part of Ser. No. 673,302, Jun. 28, 1996, abandoned.

[51] Int. Cl.$^6$ .................................................. A41D 19/00
[52] U.S. Cl. .......................... 2/168; 2/161.6; 2/161.7; 2/167; 427/2.3; 428/423.9; 428/424.2; 428/424.7; 428/424.8; 428/425.5; 428/451; 428/492; 428/521; 428/522
[58] Field of Search ............................ 2/161.6, 161.7, 2/167, 168; 427/2.3; 428/423.1, 423.9, 425.5, 451, 492, 521, 522, 424.2, 424.7, 424.8

[56] References Cited

U.S. PATENT DOCUMENTS

| | | | |
|---|---|---|---|
| 3,251,905 | 5/1966 | Zelinski | 525/272 |
| 3,265,765 | 8/1966 | Holden et al. | 525/271 |
| 3,268,593 | 8/1966 | Carpenter et al. | 568/616 |
| 3,293,191 | 12/1966 | Carpenter et al. | 252/351 |
| 3,390,207 | 6/1968 | Moss et al. | 525/271 |
| 3,411,982 | 11/1968 | Kavalir et al. | 428/493 |
| 3,598,887 | 8/1971 | Darcy et al. | 525/271 |
| 3,639,521 | 2/1972 | Haieh | 525/98 |
| 3,740,262 | 6/1973 | Agostinelli | 427/2.3 |
| 3,813,695 | 6/1974 | Podell, Jr. et al. | 2/168 |
| 3,856,561 | 12/1974 | Esemplare et al. | 428/494 |
| 3,905,823 | 9/1975 | Piskoti | 106/38.22 |
| 3,992,221 | 11/1976 | Homsy et al. | 134/16 |
| 4,070,713 | 1/1978 | Stockum | 2/168 |
| 4,143,109 | 3/1979 | Stockum | 264/112 |
| 4,208,356 | 6/1980 | Fukawo et al. | 525/89 |
| 4,219,627 | 8/1980 | Halasa et al. | 525/89 |
| 4,302,852 | 12/1981 | Joung | 2/167 |
| 4,310,928 | 1/1982 | Joung | 2/161 |
| 4,482,577 | 11/1984 | Goldstein et al. | 427/2 |
| 4,499,154 | 2/1985 | James et al. | 428/494 |
| 4,575,476 | 3/1986 | Podell et al. | 428/494 |
| 4,597,108 | 7/1986 | Momose | 2/168 |
| 4,690,955 | 9/1987 | Kilgour et al. | 521/112 |
| 4,769,174 | 9/1988 | Kilgour | 252/351 |
| 4,847,398 | 7/1989 | Mehta et al. | 556/445 |
| 4,851,266 | 7/1989 | Momose et al. | 427/353 |
| 4,857,583 | 8/1989 | Austin et al. | 524/761 |
| 5,284,607 | 2/1994 | Chen | 264/37 |
| 5,395,666 | 3/1995 | Brindle | 429/36.4 |
| 5,405,666 | 4/1995 | Brindle | 428/36.4 |
| 5,612,083 | 3/1997 | Haung et al. | 264/233 |

FOREIGN PATENT DOCUMENTS

| | | |
|---|---|---|
| 365547 | 1/1932 | United Kingdom. |
| 1254093 | 11/1971 | United Kingdom. |
| 8100361 | 2/1981 | WIPO. |

OTHER PUBLICATIONS

"Special Report; Raw Materials; Additives," *Chemical Week*, Oct. 12, 1994; p. 46.
"Product Array Broadens; Demand, For High Performance Rises," by Esther D'Amico, *Chemical Week*, Oct. 11, 1995, p. 39.
"OSI Specialties, Inc.: a New Global Company Brings Over Four Decades of Leadership to the Nonwovens Finishing Marketplace; 12th Annual International Show in Print," *Nonwovens Industry*, May 1994, vol. 25; No. 5; p. 100.
"The Importance of Low Dynamic Surface Tension in Waterborne Coatings," by Joel Schwartz, *Journal of Coatings Technology*, Sep. 1992 (11 pages plus cover page).
*High Polymer Latices*, by D. C. Blackley, vol. 2, Testing and Applications, Palmerton Publishing Co. Inc. 1966, p. 548.
*Neoprene Latex*, by John Carl, E.I. DuPont, Wilmington, DE, 1962 (one page).
Technical Summary Sheet—Zeneca: NeoRez XR–9624, Experimental Water–borne Polyruethane, Revised Jan. 1994 (4 pages).
Material Safety Data Sheet—Sigma Chemical Company: Cetylpyridinium Chloride Crystalline (5 pages), Apr. 27, 1995.
Material Safety Data Sheet—OSi Specialities, Inc.: NUWET 300, Feb. 9, 1995 (5 pages).
Technical Summary Sheet—Air Products and Chemicals, Inc.: Dynol* 604 Surfactant (9 pages), Feb. 1995.
Technical Summary Sheet—OSi Specialties: NuWet Durable Hydrophilic Finishes for Nonwovens (14 pages), May 1996.

(List continued on next page.)

Primary Examiner—D. S. Nakarani
Attorney, Agent, or Firm—Baker & Botts, L.L.P.

[57] ABSTRACT

In accordance with the present invention, there is provided a flexible article, such as a surgeon's glove, displaying slip properties with respect to damp and dry mammalian tissue without use of powder lubricants. The article is comprised of a substrate layer having an elastomeric material, the layer having a wearer-contacting surface and a damp slip-conferring amount of a lubricant composition applied to the wearer-contacting surface. The lubricant composition is selected from the group consisting of a first composition and a second composition. The first composition comprises an acetylenic diol and at least one compound selected from the group consisting of an organo-modified silicone, an amino-modified silicone, and a cationic surfactant. The second composition comprises a cationic surfactant and at least one compound selected from the group consisting of an organo-modified silicone, an amino-modified silicone, and an acetylenic diol. The elastomer may be natural or synthetic, and is preferably selected from the group consisting of natural rubber, a polyurethane, neoprene, nitrile rubber, a styrene-butadiene-styrene block copolymer, a styrene-isoprene-styrene block copolymer and combinations thereof. The cationic surfactant is preferably 1-hexadecylpyridinium chloride monohydrate.

20 Claims, No Drawings

OTHER PUBLICATIONS

Technical Summary Sheet—OSi Specialties: NuWet Hydrophilic Silicone Finishes Using Aqueous and Nonaqueous Diluents (30 pages), May 1996.

Material Safety Data Sheet—Van Waters & Rogers Inc., Subsidiary of Univar: Silicone Emulsion LE–46, pp. 1–4), Jan. 29, 1990.

Material Safety Data Sheet—Zeneca: NeoRaz R–962 (3 pages), May 25, 1994.

"Acetylenic Diol–Based Additives Help Glove Makers Meet Quality Standards," by Joel Schwartz and William R. Dougherty, *Elastomerics*, Dec. 1989, pp. 16–18.

"Antifoam, Plastics, Additives and Other Processes," *Silicones*, vol. II, Chemical Technology Review No. 92, 1977, pp. 344–347 plus cover page.

The Vanderbilt Latex Handbook, edited by Robert Francis Mausser, Third Edition, Published by R. T. Vanderbilt Company, Inc., 1987, pp. 208–210.

SLIP-COATED ELASTOMERIC FLEXIBLE ARTICLES AND THEIR METHOD OF MANUFACTURE

This application is a Continuation-in-Part of U.S. application Ser. No. 08/673,302, filed on Jun. 28, 1996, now abandoned, and entitled "Slip-Coated Elastomeric Flexible Articles and Their Method of Manufacture".

TECHNICAL FIELD OF THE INVENTION

This invention relates to elastomeric flexible articles (e.g., film articles), particularly powder-free medical gloves, that exhibit enhanced lubricity ("slip") with respect to both dry and damp surfaces, particularly skin or other tissue of the wearer, as compared to similar articles or films that are not treated as described herein. This invention also relates to a process for making such articles. This invention further relates to a lubricant composition and a method of treating elastomeric flexible articles with a lubricant composition.

BACKGROUND OF THE INVENTION

Elastomeric surfaces of articles, in general, exhibit poor lubricity with respect to a dry surface, such as dry skin or other mammalian tissue. These properties are due to surface friction. Additionally, many elastomeric articles or surfaces display poor lubricity with respect to damp surfaces. A high coefficient of friction is a distinct disadvantage in those applications where an elastomeric surface must slide on another surface, such as in the donning of gloves over dry or damp skin. This is particularly important in the use of medical gloves, such as examination gloves and surgeon's glove. These gloves are relatively close fitting in order to provide sensitivity. Further, most surgeons don their gloves after scrubbing up and without having fully dried their hands, so that their hands may be distinctly damp. Accordingly, the elastomeric materials useful in such applications must exhibit enhanced lubricity with respect to dry surfaces ("dry slip"), enhanced lubricity with respect to damp surfaces ("damp slip"), and the requisite mechanical properties. The prior art has attempted various ways to produce powderless gloves which satisfy these requirements.

One prior approach is to halogenate the surface of rubber gloves with chlorine or bromine to make it slippery, i.e., reducing tackiness and decreasing the coefficient of friction of the rubber gloves. In the case of chlorine as the halogen, the prior art discloses the production and use of chlorinated water to treat the rubber gloves. Such methods include (1) direct injection of chlorine gas into the water mixture, (2) mixing high density bleaching powder and aluminum chloride in water, (3) brine electrolysis to produce chlorinated water, and (4) acidified bleach. See for example U.S. Pat. Nos. 3,411,982 (Kavalir), 3,740,262 (Agostinelli), 3,992,221 (Homsy, et al.; treating outer surface with chlorine gas), 4,597,108 (Momose), and 4,851,266 (Momose). However, chlorination produces surfaces which have very poor damp slip.

There are other prior rubber gloves having a slip layer bonded to the inner surface of such gloves. Examples of gloves which have an inner layer of elastomeric material with particulate lubricant imbedded therein are disclosed in U.S. Pat. Nos. 4,070,713 (Stockum), 4,143,109 (Stockum), 5,284,607 (Chen) and 5,395,666 (Brindle; together with a surfactant, but ionic surfactants are not recommended), and which disclose surgeon's gloves with various polymeric slip coatings bonded to the inner surface thereof are U.S. Pat. Nos. 3,813,695 (Podell, et al.; an inner layer of hydrophilic plastic material, e.g., hydrogel polymer), 3,856,561 (Esemplare, et al.; an inner layer of a copolymer of vinyl or vinylidene chloride and an alkyl acrylate), 4,302,852 (Joung), 4,482,577 (Goldstein, et al.), 4,499,154 (James, et al.; uses specific hydrogel polymers as the inner layer which is then treated with a cationic surfactant or fatty amine) and 4,575,476 (Podell, et al.; hydrogel polymer inner layer treated with cationic, anionic or nonionic surfactant). The foregoing differ from the present invention.

SUMMARY OF THE INVENTION

In accordance with the present invention, there is provided a flexible article displaying slip properties with respect to damp and dry mammalian tissue without use of powder lubricants. The article is comprised of a substrate layer having an elastomeric material, the layer having a wearer-contacting surface and a damp slip-conferring amount of a lubricant composition applied to the wearer-contacting surface. The lubricant composition is selected from the group consisting of a first composition and a second composition, wherein the first composition comprises an acetylenic diol and at least one compound selected from the group consisting of an organo-modified silicone, an amino-modified silicone, and a cationic surfactant, preferably 1-hexadecylpyridinium chloride monohydrate, and wherein the second composition comprises a cationic surfactant, preferably 1-hexadecylpyridinium chloride monohydrate, and at least one compound selected from the group consisting of an organo-modified silicone, an amino-modified silicone, and an acetylenic diol.

In one embodiment, the article is a surgeon's glove. The elastomer may be natural or synthetic, and is preferably selected from the group consisting of natural rubber, a polyurethane, a homopolymer of a conjugated diene, a copolymer of at least two conjugated dienes, a copolymer of at least one conjugated diene and at least one vinyl monomer and combinations thereof. The conjugated diene may contain hetero atoms, such as conjugated dienes which have been halogenated, e.g., chloroprene. Preferred conjugated dienes include butadiene, isoprene and chloroprene. Preferred vinyl monomers include alkenyl arenes, e.g., styrene, alkylenes, e.g., ethylene and propylene, and acrylonitrile. The term "combinations thereof" in regard to the elastomer includes physical combinations thereof in a single layer and layered combinations thereof, for example, a multi-layered elastomeric article having a layer of polyurethane formed over and adhering to a layer of natural rubber.

There is also provided a method of treating an elastomeric flexible article. The method comprises: (a) cleaning the article surface by washing; (b) chlorinating the article surface; (c) neutralizing the article surface and residual chlorine; and (d) treating the article surface with a lubricant composition.

The lubricant composition is selected from a first composition and a second composition, wherein the first composition comprises an acetylenic diol and at least one compound selected from the group consisting of an organo-modified silicone, an amino-modified silicone, and a cationic surfactant, preferably 1-hexadecylpyridinium chloride monohydrate (also known as cetylpyridinium chloride), and wherein the second composition comprises a cationic surfactant, preferably 1-hexadecylpyridinium chloride monohydrate, and at least one compound selected from the group consisting of an organo-modified silicone, an amino-modified silicone, and an acetylenic diol.

If the article has previously been chlorinated or does not require or permit chlorination, steps (b) and (c) may be eliminated. If a powder is not used as a mold release when the articles are made, the washing step (a) may be eliminated.

Medical powder-free gloves treated with the lubricant composition provide superior lubricity with respect to wet/damp donning in comparison to the current chlorinated surgical gloves in the market.

DETAILED DESCRIPTION OF THE INVENTION

The invention envisages flexible elastomeric articles including those adapted for use in partial or total contact with mammalian tissue, such as surgical, examination and dental gloves, condoms, bandages, catheters, ureters, sheathes and sheath-type incontinence devices and other film articles. Additionally, the damp/dry slip-conferring materials may be provided on one or more surfaces of the article including, but not limited to, an inner and/or outer surface relative to the wearer, as appropriate under the circumstances of the use of each article.

For purposes of this description, the outer surface of an article and, in particular, a glove, is defined as that surface which becomes an external surface of the glove in the position of actual use when worn. The inner surface is defined as that surface which is adjacent to the skin of the wearer when worn. The reverse is true in the case of a catheter or ureter: the outer surface is the surface in contact with the wearer's tissue. To avoid ambiguity, the term "wearer-contacting surface" will be used herein. "Tissue" includes skin or epithelia without limitation.

The elastomer used in the substrate layer may be a natural or synthetic rubber. Without limitation, synthetic rubbers include polyurethane, a homopolymer of a conjugated diene, a copolymer of at least two conjugated dienes, a copolymer of at least one conjugated diene and at least one vinyl monomer, and combinations thereof.

The conjugated dienes are preferably ones containing from 4 to 8 carbon atoms. Examples of such suitable conjugated dienes include: 1,3-butadiene (butadiene), 2-methyl-1,3-butadiene (isoprene), 2,3-dimethyl-1,3-butadiene, 1,3-pentadiene (piperylene), 1,3-hexadiene, and the like. The conjugated dienes may contain hetero atoms. Such conjugated dienes include those which have been halogenated, for example, chloroprene. Mixtures of such conjugated dienes may also be used. The preferred conjugated dienes are butadiene, isoprene and chloroprene.

Any vinyl monomer may be used for copolymerization with at least one conjugated diene to prepare synthetic rubbers so long as the resulting copolymer is elastomeric. Without limitation, such vinyl monomers include alkylenes, alkenyl arenes, and acrylonitrile. The preferred alkylenes are ethylene, propylene and butylenes. The preferred alkenyl arenes are monoalkenyl arenes. The term "monoalkenyl arene" will be taken to include particularly those of the benzene series such as styrene and its analogs and homologs including o-methylstyrene, p-methylstyrene, p-tert-butylstyrene, 1,3-dimethylstyrene, alpha-methylstyrene and other ring alkylated styrenes, particularly ring-methylated styrenes, and other monoalkenyl polycyclic aromatic compounds such as vinyl naphthalene, vinyl anthracene and the like. The preferred monoalkenyl arenes are monovinyl monocyclic arenes such as styrene and alpha-methylstyrene, and styrene is particularly preferred.

The copolymers may be random, tapered or block copolymers. If the copolymers are block copolymers, it will be understood that each of the blocks thereof may be a homopolymer, a random copolymer or a tapered copolymer as long as each block predominates in at least one class of the monomers characterizing the block. For example, blocks of alkenyl arenes may comprise styrene/alpha-methylstyrene copolymer blocks or styrene/butadiene random or tapered copolymer blocks as long as the blocks individually predominate in alkenyl arenes.

Preferred rubbers are natural rubber and synthetic rubbers, including polyurethane, neoprene, nitrile rubber, block copolymers of styrene and butadiene, particularly a styrene-butadiene-styrene block copolymer, and block copolymers of styrene and isoprene, particularly a styrene-isoprene-styrene block copolymer. Natural rubber and polyurethane are more preferred, with natural rubber being most preferred. Neoprene is a homopolymer of the conjugated diene chloroprene. Nitrile rubber is a copolymer of the conjugated diene butadiene and the vinyl monomer acrylonitrile.

The block copolymers of alkenyl arenes ("A" blocks) and conjugated diene ("B" blocks) are preferably network forming, i.e., at least two A blocks and at least one B block. The simplest form of such a block copolymer is A-B-A, which is a triblock copolymer. In such a synthetic rubber, the A blocks are thermodynamically incompatible with the B block(s) resulting in a rubber consisting of two phases; a continuous elastomeric phase (B blocks) and a basically discontinuous hard, glass-like plastic phase (A blocks) called domains. These domains act as physical crosslinks anchoring the ends of many block copolymer chains. Since the A-B-A block copolymers have two A blocks separated by a B block, domain formation results in effectively locking the B blocks and their inherent entanglements in place by the A blocks and forming a network structure. Such a phenomenon allows the A-B-A rubber to behave like a conventionally vulcanized rubber that contains dispersed reactive filler particles. These thermoplastic A-B-A rubbers are physically crosslinked by the domains in a network structure as opposed to being chemically crosslinked like a conventionally vulcanized rubber. As such, these polymers may be handled in thermoplastic forming equipment and are soluble in a variety of relatively low cost solvents. Additionally, when polymers of this type are used, the vulcanization step may be eliminated and, contrary to vulcanized scrap rubbers, the scrap from the processing of these thermoplastic elastomers can be recycled for further use.

The block copolymers may be produced by any well known block polymerization or copolymerization procedures including the well known sequential addition of monomer techniques, incremental addition of monomer technique or coupling technique as illustrated in, for example, U.S. Pat. Nos. 3,251,905; 3,390,207, 3,598,887 and 4,219,627, the disclosures of which are incorporated herein by reference. As is well known in the block copolymer art, tapered copolymer blocks can be incorporated in the multiblock copolymer by copolymerizing a mixture of conjugated diene and alkenyl arene monomers utilizing the difference in their copolymerization reactivity rates. Various patents describe the preparation of multiblock copolymers containing tapered copolymer blocks including U.S. Pat. Nos. 3,251,905; 3,265,765; 3,639,521 and 4,208,356, the disclosures of which are incorporated herein by reference.

It should be observed that the above-described polymers and copolymers may, if desired, be readily prepared by the methods set forth above. However, since many of these polymers and copolymers are commercially available, for example, KRATON™ polymers available from Shell Oil Company, it is usually preferred to employ the commercially available polymer as this serves to reduce the number of processing steps involved in the overall process.

Typical thicknesses of the elastomeric substrate layer for surgical gloves range from about 30 to about 400 microns, preferably from about 100 to about 350 microns. Surgical gloves tend to be about 150 microns thick and orthopedic gloves tend to be about 300 microns thick.

To impart damp slip properties to the flexible elastomeric article, which is at least substantially powderless and is preferably chlorinated, the article is treated with a lubrication composition. There are two suitable combinations of components. The first composition comprises (i.e., having at least) (1) an acetylenic diol and (2) at least one compound selected from the group consisting of an organo-modified silicone, an amino-modified silicone, and 1-hexadecylpyridinium chloride monohydrate. The second composition comprises (1) 1-hexadecylpyridinium chloride monohydrate and (2)at least one compound selected from the group consisting of an organo-modified silicone, an amino-modified silicone, and an acetylenic diol. The lubricant composition is preferably an aqueous solution or dispersion.

The compound 1-hexadecylpyridinium chloride monohydrate (CAS No. 6004-24-6) is a commercially available cationic surfactant. Other suitable cationic surfactants include those comprising at least one lipophilic moiety such as an alkyl, aralkyl, aryl, or cycloalkyl group containing 6 to 18 carbon atoms, and a hydrophilic moiety such as a substituted ammonium group (for example, a tetraalkylammonium, pyridinium, or like group). The counterion present should be compatible with the tissue of the wearer; it could be, for example, chloride or other halide.

Preferred cationic surfactants are quaternary ammonium compounds having at least one $C_8$–$C_{18}$ hydrocarbyl (alkyl, aryl, aralkyl or cycloalkyl) group; a preferred hydrocarbyl group is a hexadecyl group. The hydrocarbyl group may be attached to a quaternary nitrogen atom which is part of a heterocyclic ring (such as a pyridine, morpholine, or imidazoline ring).

As previously mentioned, a particularly preferred surfactant is hexadecylpyridinium chloride. Other suitable cationic surfactants include benzalkonium chlorides, hexadecyltrimethylammonium chloride, dodecylpyridinium chloride, the corresponding bromides, a hydroxyethylheptadecylimidazolium halide, coconut alkyldimethylammonium betaine and coco aminopropyl betaine.

Mixtures of surfactants may also be used.

The cationic surfactant, e.g., the preferred cetylpyridinium chloride, concentration is in the range from about 0.05% to about 2.5% by weight. A range from about 0.25% to about 0.75% by weight, for example, 0.5%, cetylpyridinium chloride solution is preferred.

The acetylenic diols useful in the present invention are acetylenic tertiary glycols and the ethylene oxide adducts of acetylenic tertiary glycols. Preferably, the acetylenic diols used in the practice of the invention are structurally represented by the formula:

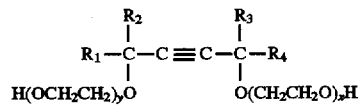

in which $R_1$ and $R_4$ are alkyl radicals containing from 3–10 carbon atoms, and $R_2$ and $R_3$ are selected from the group consisting of methyl and ethyl, and x and y have a sum in the range of 0–60, inclusive, where y=x=0 represents the acetylenic tertiary glycols. In the preferred case, $R_1$ and $R_4$ are alkyl radicals having 3–4 carbon atoms each and $R_2$ and $R_3$ are methyl groups. Further examples and synthesis techniques for the manufacture of these acetylenic diols are disclosed in U.S. Pat. Nos. 3,268,593 (Carpenter et al.) and 3,293,191 (Carpenter et al.), which are hereby incorporated by reference.

Acetylenic diols useful in the present invention preferably have a 10-carbon chain as a backbone with a carbon-carbon triple bond in the middle with a hydroxyl group on the carbon atoms on either side of the triple bond. The combination of these groups yields a region of high electron density, making the molecule polar. There is also a symmetrical, highly branched group on each side of this region supplying the molecule with two hydrophobic areas. Overall the molecule has a hydrophobic-hydrophilic-hydrophobic structure, making it a good wetting agent or surface tension reducer. See J. Schwartz et al., "Acetylenic diol-based additives help glove makers meet quality standards," Elastomerics, pages 16–18, December 1989. Suitable acetylenic diols include the following available from Air Products and Chemicals, Inc., Allentown, Pa: Surfynol® 104 (2,4,7,9-tetramethyl-5-decyn-4,7-diol), Surfynol® 104E (Surfynol® 104/ethylene glycol, 50/50), Surfynol® 440 (Surfynol® 104+3.5 moles ethylene oxide), Surfynol® 465 (Surfynol® 104+10 moles ethylene oxide) and Dynol® 604 (a mixture of ethoxylated acetylenic diols).

The acetylenic diols are preferably ethoxylated acetylenic diols such as Dynol® 604 and Surfynol® 400 series available from Air Products and Chemical Inc., Allentown, Pa. Dynol® 604 is preferred because it provides better lubricity. The acetylenic diol is used in the form of a solution, such as an aqueous solution containing at least 0.01% by weight up to, for example, 2% by weight of acetylenic diols. The acetylenic diols may be used in a mixture or combination.

The modified silicones useful in the present invention are hydrophilic, nonionic silicones. Examples of such silicones are commercially available from OSi Specialties, Inc., Danbury, Conn. are NuWet® 100, NuWet® 300 and NuWet® 500. NuWet® 100 is a copolymer described as an organo-modified polydimethylsiloxane, more specifically a polyalkylene oxide modified polydimethylsiloxane. NuWet® 300 is also a copolymer described as an amino-modified silicone-polyether copolymer. As a result of the amino-modification, this material has reportable quantities of an alkanolamine. NuWet® 500 is a blend of an organo-modified polydimethylsiloxane (>65%) and an ethoxylated alkyl (<20%). There are reportable quantities of ethylene oxide (<20%; upper bound concentration per MSD Sheet is 0.0002%). The following Table provides some physical properties for these three materials.

| Physical Property | NuWet® 100 | NuWet® 300 | NuWet® 500 |
|---|---|---|---|
| Appearance | Clear | Clear–Sl. Haze | Clear |
| Color | Lt. Straw | Lt. Straw to Tan | Colorless to Lt. Straw |
| Nominal Viscosity, cP | 425 | 3500 | 400 |
| Solubility in Water | Soluble | Dispersable | Dispersable |
| Ionic Nature | Non-ionic | Non-ionic | Non-ionic |
| % Actives | 100 | 100 | 100 |

| Physical Property | NuWet ® 100 | NuWet ® 300 | NuWet ® 500 |
|---|---|---|---|
| Density | 1.06 | 1.027 | 1.02 |
| Flash Point* | 175° F. | 230° F. | 285° F. |
| Freezing Point | −9.4° F. | <32° F. | <32° F. |
| Molecular Weight | Copolymer | Copolymer | Copolymer |

*Pensky-Martens closed cup ASTM D-93.

According to OSi's product bulletin, the following non-aqueous diluents have been found useful:

ethylene-propylene oxide polymers (Ucon 50HB 100, Union Carbide)

methyl soyate (Emery 2235, Henkel)

methyl oleate (Emerest 2301, Henkel)

methyl cannolate (Emery 2231, Henkel)

propylene carbonate (Arco)

oleyl alcohol (Novol, Croda)

When preparing aqueous solutions or dispersions with these materials, OSi recommends pouring the silicone into the vortex of the total water while mixing at a moderate speed (about 300 rpm to about 400 rpm). Mixing is continued until a uniform solution or dispersion is obtained. Non-aqueous solutions or dispersions are prepared in a similar manner, but mix at about 150 rpm to about 200 rpm until a clear mixture is obtained.

U.S. Pat. Nos. 4,690,955 (Kilgour et al.); 4,769,174 (Kilgour);4,847,398 (Mehta et al.) and 4,857,583 (Austin et al.), disclose various organo-modified polysiloxane copolymers (i.e., organo-modified silicones) and methods of making same. Such copolymers contain hydroxyl groups. The amino-modification may be performed by first substituting a halide for the hydroxyl group. The halide may then be reacted with ammonia or an amine to substitute an amino group for the halide. This latter process is called ammonolysis of halides. Alternatively, amino-modified polysiloxanes (i.e., amino-modified silicones) may be prepared according to U.S. Pat. No. 3,905,823 (Piskoti), which is hereby incorporated by reference. Therein the amino-modified polysiloxanes are prepared by mixing an organo-modified polysiloxane (i.e., organo-modified silicone) with amino-functional silanes or siloxanes and thereafter equilibrating the mixture in the presence of a base catalyst, e.g., alkali metal hydroxides, alkoxides, hydrides, alkyls, alkenyls and aryls, and silanoates.

The modified silicone is generally used in the form of a solution, such as an aqueous solution containing at least 0.05% by weight up to, for example, 5% by weight of the modified silicone.

The coating of lubricant composition need not coat the wearer-contacting surface completely. It is only necessary that enough lubricant composition is applied to enhance damp slip. It is preferred, to the extent that it is practicable, to keep the lubricant composition on the wearer-contacting surface, in the case of medical or dental gloves, in order to ensure that maximum grip is maintained on the outer surface. The lubricant composition can be applied as an aqueous solution containing from about 0.2 to about 2% by weight lubricant composition total. The article can be dipped in such solution or the solution can be sprayed or painted on it, preferably before it is removed from the form. Alternatively, the lubricant composition can be applied after the article is stripped from the form.

The process for applying the particle-containing coating to the wearer-contacting surface of the elastomer substrate depends, in part, on the nature of the substrate and on whether the glove or other article is formed by dipping a form into an elastomeric polymer latex or into a solution of the elastomeric polymer in a suitable solvent. Methods for making the elastomeric substrate articles of the present invention are well known in the art.

Where the article is formed from compounded natural rubber latex, the deposit on the form is beaded and leached in the normal way and may then be dried and vulcanized. It is envisaged that the coating will normally be applied by subsequently dipping the deposit on the form into an aqueous suspension of the coating material, i.e., the binder and microparticles. The deposit and coating may then be heated to dry them and to complete vulcanization of the rubber.

Other substrate polymers in dispersed, e.g., latex, form, including polyurethanes, may be treated similarly, although a vulcanizing step will not be needed in every case, as can be readily appreciated by those skilled in the art.

It is understood that various optional ingredients may be incorporated in these articles as apparent to those skilled in the art. For example, where the article is a glove, an antiblock agent may be used which would facilitate donning and use. The antiblock agent is preferably a low-melting wax (mp. from about 100° C. to about 150° C.) such as polyethylene wax added as an aqueous emulsion (e.g., 1–2%) to the coating mixture. The particle size of the wax should be preferably less than 1 µm to avoid interference with the surface morphology.

In accordance with the present invention, an embodiment of a continuous process for making a powder-free glove comprises in summary form:

(i) dip-coating a coagulant onto a glove form;

(ii) dip-coating over the coagulant layer a layer of an elastomer;

(iii) leaching the elastomer article in the hot water;

(iv) heat curing the elastomer;

(v) chlorinating the glove;

(vi) neutralizing the glove and residual chlorine;

(vii) rinsing the glove;

(viii) treating the glove with a lubricant composition;

(ix) drying the lubricant treated glove; and (x) removing the glove from the form, thereby reversing the glove.

If the elastomer is not to be chlorinated, steps (v)–(vii) can be omitted.

In accordance with the present invention, another embodiment of the process for making a powder-free glove comprises in summary form:

(a) General process for making powdered gloves by (i) dip-coating a coagulant onto a glove form;

(ii) dip-coating over the coagulant layer a layer of an elastomer;

(iii) leaching the elastomer article in the hot water;

(iv) heat curing the elastomer;

(v) dip-coating a starch slurry onto the cured elastomer; and (vi) removing the glove from the form and reversing the glove.

(b) Off-line chlorination of the powdered glove followed by treatment with the lubricant composition.

(i) inverting and washing the powdered glove;

(ii) chlorinating the glove;

(iii) neutralizing the glove and residual chlorine;

(iv) rinsing the glove;

(v) treating the glove with a lubricant composition;

(vi) drying the lubricant treated glove; and (vii) inverting and re-drying the glove.

The application of the lubricant solution provides the chlorinated powder-free glove with superior lubricity with respect to wet/damp hand donning. The steps of part (a) may be omitted if powdered gloves are available. Likewise, if chlorinated gloves are available, steps (b)(ii)–(iv) may be omitted.

In an expanded manner, the steps for one embodiment of the present invention are discussed below. First there is a cleaning step to clean for example the hand form, typically made of porcelain, to remove residue from previous manufacturing iterations. The clean form is then dried to remove water residue by conveying the form through a preheated oven to evaporate the water.

The preheated form is then dip-coated in a bath containing a coagulant, a powder source and a surfactant. The coagulant preferably contains calcium ions to break the protection system of the emulsion, thereby allowing the latex to deposit on the form. The powder is preferably a calcium carbonate powder which later acts as a release agent. Alternatively, the powder source may be omitted by using the lipo compound and surfactant combination in the coagulant to aid in stripping the glove according to U.S. Pat. No. 4,310,928 to Jourg. The surfactant provides good wetting to avoid forming a meniscus and trapping air between the form and deposited latex, particularly in the cuff area. An example of such a surfactant is an acetylene diol. As noted above, the form has been preheated in the drying step and the residual heat dries off the water leaving calcium nitrate, calcium carbonate powder and surfactant on the surface of the form.

The coated form is then dipped into a latex containing tank. The latex contains for example, natural rubber latex plus stabilizers, antioxidant, activators, accelerators, and vulcanizers, and the latter all being in powder form. The stabilizers are preferably of the phosphate type surfactants. The antioxidants are preferably the phenol type, for example, Antioxidant 2246 (2,2'-methylenebis (4-methyl-6-t-butylphenol)) available from PMC Specialty Group, Fords, N.J. The activator may be for example zinc oxide. The accelerator may be for example dithiocarbamate. The vulcanizer is preferably sulphur or a sulphur-containing compound. If these materials are used, the stabilizer, antioxidant, activator, accelerator and vulcanizer are dispersed into water to avoid crumb formation by using a ball mill or an attritor. This dispersion is then mixed into the latex. An emulsified wax, which is used as an antiozonant, is then added to the latex mixture. The coated form is then dipped into the latex composition with the thickness of the latex deposited thereon controlled by the duration of the dip (in a single dip situation). This is about 5 to about 20 seconds, e.g., about 12 seconds, for a surgical glove; and about 20 to about 70 seconds, e.g., about 50 seconds, for an orthopedic glove.

The form now coated with latex is then dipped into a leaching tank in which hot water is circulated to leach out all water soluble components for example residual calcium nitrates and proteins contained in the natural latex. This leaching process may continue for about twelve minutes with the tank water being about 120° F.

The form is then extracted from the leach bath to a bead and print station. At this station, a bead is formed around the cuff area at the end of the glove by mechanically rolling down the top portion or the end portion of the glove a predetermined amount. Company logos, size and a traceable date of manufacture are then printed onto the exterior of the glove, for example by injecting ink into the latex coating on the form.

The latex coated form is then sent to a curing station where the natural rubber in the form coating is vulcanized typically in an oven, thereby heat curing the rubber. The curing station initially evaporates any remaining water in the latex coating of the form and then proceeds to the higher temperature vulcanization. The drying may occur between 190° F. to 200° F. with a vulcanization step occurring at temperatures for example from about 220° F. to about 240° F. This overall process may last about forty to forty-five minutes total. For example, the oven may be divided into four different zones with a form being conveyed through the zones of increasing temperature. One example is an oven having four zones with the first two zones being dedicated to drying and the second two zones being primarily the vulcanization step. Each of the zones may have a slightly higher temperature, for example, the first zone at about 180° F., the second zone at about 200° F., a third zone at about 220° F. and a final zone at about 240° F. The residence time of the form within a zone in this case is about ten minutes or so. The accelerator and vulcanizer contained in the latex coating of the form are used to cross-link the natural rubber therein. The vulcanizer forms sulphur bridges between different rubber segments and the accelerator is used to speed up sulphur bridge formation.

The form now having a cured rubber glove thereon is then dipped into a starch slurry. Conventional powder-containing gloves may be withdrawn and packaged at this point. The slurry has starch and silicone to improve donning of the conventional glove on a person's hand, for example. The starch is preferably epichlorohydin cross-linked starch. The silicone is also used to try to prevent blocking during stripping of the glove from the form and to help donning of a dry hand. Therefore, the glove will have a starch powder on the surface which is loosely attached thereto. Next, the glove is stripped from the form which inverts the glove with the inside now being out and vice versa. The gloves are then sorted by sizes and inspected for suitability.

The foregoing steps are those which are used in making a prior art powder-containing glove to aid in the donning of a user's hand. Rather than making these gloves, such prior art gloves may be obtained and then treated in the following manner.

These powdered gloves are then inverted again inside out and accordingly is in the orientation the glove was in prior to stripping from the form.

The inverted glove is then washed to remove the powder and starch from the glove. The wash is performed with ambient temperature tap water and may be repeated as necessary.

The washed gloves are then chlorinated. If a continuous process is used, the cured gloves leaving the curing station and optionally still on the form are then chlorinated and the intervening steps omitted. The chlorination, or more generally halogenation, may be performed in any suitable manner known to those skilled in the art. Such methods include (1) direct injection of chlorine gas into the water mixture, (2) mixing high density bleaching powder and aluminum chloride in water, (3) brine electrolysis to produce chlorinated water, and (4) acidified bleach. See for example U.S. Pat. Nos. 3,411,982 (Kavalir), 3,740,262 (Agostinelli), 3,992,221 (Homsy, et al.; however, it is modified to treat the wearer-contacting surface rather than or in addition to treating outer surface with chlorine gas), 4,597,108 (Momose), and 4,851,266 (Momose). One preferred method is to inject chlorine gas into a water stream and then feed the chlorinated water into a chlorinator (a closed vessel) containing the washed gloves. The concentration of chlorine can be monitored and controlled to control the degree of chlorination. The chlorine concentration is typically at least about 500 ppm, preferably from about 500 ppm to about 1,200 ppm, e.g., about 800 ppm. The time duration of the chlorination step may also be controlled to control the degree of chlorination. The time duration may range from about 3 to about 20 minutes, e.g., 7 minutes. The gloves being in a collapsed state will chlorinate to a greater extent on the wearer-contacting surface, i.e., the donning side of the glove, with a lesser amount on the non-donning side of the glove.

In another preferred method, the gloves may be chlorinated by placing them into a chlorinator, including a front-loaded industrial washer, containing a water bath which contains bleach which is subsequently acidified to a pH of 2 to about 3. The chlorine concentration ranges from about 0.05 to about 0.3 wt. %, e.g., about 0.1 wt. %. The time duration ranges from about 3 to about 25 minutes. Again, the donning side of the glove will have a greater amount of chlorination than the non-donning side of the glove. For a greater degree of chlorination on the non-donning side of the glove, the gloves would have to be reinverted and the chlorination step repeated.

The acidified bleach is then neutralized preferably with ammonium hydroxide or with sodium thiosulfate. This step neutralizes the acidified water contained in the chlorinator and quenches excess chlorine to ammonium chloride, if ammonium hydroxide is used.

Still within the industrial washer, the chlorinated gloves are then rinsed with tap water at about ambient temperature. This rinse cycle may be repeated as necessary. Once all water is removed from the front-load washer, the gloves are tumbled to drain excess water.

A lubricant solution is then added into the chlorinator containing gloves which are then tumbled for about five minutes. This coats the donning side with the lubricant solution. The lubricant solution is drained from the chlorinator and may be reused. If reused, the lubricant solution is preferably reused once more.

The coated gloves are then put into a drier and dried for about ten to fifteen minutes at about 110° F. to dry the donning surface. The gloves are then reinverted and the non-donning side dried for about twenty-five minutes at about 120° F.

The foregoing shows a sequence of events in the manufacture of gloves according to the present invention. If powdered gloves are available or chlorinated gloves are available, some of the preceding steps may be eliminated and the process started at the appropriate step in the process.

EXAMPLES

In the following examples and comparative examples, the following additional product designations are used:

NeoRez® XR-9624 is an aliphatic polyurethane aqueous dispersion available from Zeneca Resins (formerly from ICI Resins), Wilmington, Mass.

Vedoc® VP180 is a polyester based polyurethane powder.

Example I

The powdered glove is manufactured with the general process described in the Detailed Description of the Invention section.

Off-line chlorination of the powdered glove to produce a powder-free glove is performed in the following sequence:
(1) invert and wash the powdered glove;
(2) chlorinate the washed glove;
(3) neutralize the glove and residual chlorine;
(4) rinse the chlorinated and neutralized glove;
(5) extract to remove excess water from the glove;
(6) the chlorinated glove is then treated with the following lubricant formulation:

|  | Parts by Weight |
| --- | --- |
| Water | 99.25 |
| Cetylpyridinium Chloride | 0.50 |
| NuWet ® 300 | 0.25 |

(7) after lubricant treatment, the lubricant treated glove is dried;
(8) invert and re-dry the lubricant treated glove. The finished glove is found to have no loose powder and superior lubricity with respect to wet/damp hand donning.

Example II

In accordance with the general procedure of Example I, a glove is formed utilizing the following lubricant formulation:

|  | Parts by Weight |
| --- | --- |
| Water | 99.25 |
| NuWet ® 500 | 0.50 |
| Dynol ® 604 | 0.25 |

The finished glove is found to have no loose powder and superior lubricity with respect to wet/damp hand donning.

Example III

In accordance with the general procedure of Example I, a glove is produced utilizing the following lubricant formulation:

|  | Parts by Weight |
| --- | --- |
| Water | 99.25 |
| Cetylpyridinium Chloride | 0.50 |
| NuWet ® 500 | 0.25 |

The finished glove is found to have no loose powder and superior lubricity with respect to wet/damp hand donning.

Example IV

A layer of natural rubber latex is applied to an average thickness of 150 micrometer onto a glove form which then is dipped into the following anti-blocking coating formulation:

|  | Parts by Weight |
| --- | --- |
| NeoRez XR-9624 | 285.71 |
| Deionized Water | 84.62 |
| Vedoc ® VP 180 | 18.00 |

A layer of the formulation is deposited over the layer of natural rubber latex. The layers are then cured and dipped in a starch slurry. The glove is stripped from the form in a manner that reverses the glove. A method of making a polymer coated glove suitable for use in connection with this invention is disclosed in U.S. Pat. No. 5,284,607.

Off-line chlorination and lubricant treatment of the above glove is performed in accordance with the general procedure of Example I.

The finished glove is found to have no loose powder and superior lubricity with respect to wet/damp hand donning.

The present invention has been described primarily with respect to surgeon's gloves. As earlier noted, the present invention is also applicable to other skin- or tissue-contacting flexible elastomeric articles, such as condoms, gloves used by doctors and veterinary surgeons for examination purposes (such gloves often being donned with dry hands), catheters, ureters, sheets, sheaths and sheath-type incontinence device.

When the present invention is used for articles such as ureters and catheters, the outer surface is coated with the lubricant composition (this being the wearer-contacting surface); for condoms the inner and/or outer surface may be treated with the lubricant composition.

What is claimed is:

1. A method of treating an elastomeric flexible article, the method comprising:

treating the article surface with a lubricant composition, wherein the lubricant composition is selected from the group consisting of a first composition and a second composition, wherein the first composition comprises
an acetylenic diol and
at least one compound selected from the group consisting of
an organo-modified silicone,
an amino-modified silicone, and
a cationic surfactant; and wherein the second composition comprises
a cationic surfactant and
at least one compound selected from the group consisting of
an organo-modified silicone,
an amino-modified silicone, and
an acetylenic diol.

2. A method according to claim 1, wherein the cationic surfactant is 1-hexadecylpyridinium chloride monohydrate.

3. A method according to claim 1, wherein prior to the treating step the method further comprises:

chlorinating the article surface; and neutralizing the article surface and residual chlorine.

4. A flexible elastomeric article having a wearer-contacting surface in which a lubricant composition has been applied to the wearer-contacting surface so as to provide lubricity of the surface with respect to damp skin, wherein the lubricant composition is selected from the group consisting of a first composition and a second composition, wherein the first composition comprises
an acetylenic diol and
at least one compound selected from the group consisting of
an organo-modified silicone,
an amino-modified silicone, and
a cationic surfactant; and wherein the second composition comprises
a cationic surfactant and
at least one compound selected from the group consisting of
an organo-modified silicone,
an amino-modified silicone, and
an acetylenic diol.

5. An article according to claim 4, wherein the article is a surgeon's glove.

6. An article according to claim 4, wherein the cationic surfactant is 1-hexadecylpyridinium chloride monohydrate.

7. A flexible article displaying slip properties with respect to damp and dry mammalian tissue without use of powder lubricants comprising:

a substrate layer comprising an elastomeric material, the layer having a wearer-contacting surface; and a damp slip-conferring amount of a lubricant composition applied to the wearer-contacting surface, wherein the lubricant composition is selected from the group consisting of a first composition and a second composition, wherein the first composition comprises
an acetylenic diol and
at least one compound selected from the group consisting of
an organo-modified silicone,
an amino-modified silicone, and
a cationic surfactant; and wherein the second composition comprises
a cationic surfactant and
at least one compound selected from the group consisting of
an organo-modified silicone,
an amino-modified silicone, and
an acetylenic diol.

8. An article according to claim 7, wherein the article is a surgeon's glove.

9. An article according to claim 7, wherein the cationic surfactant is 1-hexadecylpyridinium chloride monohydrate.

10. An article according to claim 7, wherein the elastomer is selected from the group consisting of natural rubber, a polyurethane, a homopolymer of a conjugated diene, a copolymer of at least two conjugated dienes, a copolymer of at least one conjugated diene and at least one monomeric compound, and combinations thereof, said monomeric compound being selected from alkenyl arenes, alkylenes, and acrylonitriles.

11. An article according to claim 10, wherein the elastomer is natural rubber.

12. An article according to claim 10, wherein the elastomer is a polyurethane.

13. An article according to claim 10, wherein the article has a first elastomeric layer and a second elastomeric layer and wherein the elastomer for the first elastomeric layer is natural rubber and the elastomer for the second elastomeric layer is polyurethane.

14. An article according to claim 10, wherein the elastomer is a homopolymer of a conjugated diene.

15. An article according to claim 14, wherein the elastomer is neoprene.

16. An article according to claim 14, wherein the conjugated diene is isoprene.

17. An article according to claim 10, wherein the elastomer is a copolymer of at least one conjugated diene and at least one monomeric compound, said monomeric compound being selected from alkenyl arenes, alkylenes, and acrylonitriles.

18. An article according to claim 17, wherein the elastomer is nitrile rubber.

19. An article according to claim 17, wherein the elastomer is a styrene-isoprene-styrene block copolymer.

20. An article according to claim 17, wherein the elastomer is a styrene-butadiene-styrene block copolymer.

* * * * *